United States Patent [19]

Jacoby et al.

[11] 4,338,826

[45] Jul. 13, 1982

[54] SAMPLING APPARATUS

[75] Inventors: Marvin Jacoby; Stuart W. Jacoby; Robert E. Jacoby; Robert A. Ellson, all of Rochester, N.Y.

[73] Assignee: Air Test Labs, Inc., Rochester, N.Y.

[21] Appl. No.: 186,168

[22] Filed: Sep. 11, 1980

[51] Int. Cl.³ .............................................. G01N 1/24
[52] U.S. Cl. ................................................. 73/864.62
[58] Field of Search ........... 73/864.62, 864.34, 864.52, 73/864.61

[56] References Cited

U.S. PATENT DOCUMENTS

| | | |
|---|---|---|
| 2,855,933 | 10/1958 | Erikson . |
| 3,017,883 | 1/1962 | Dickenson, Jr. . |
| 3,376,868 | 4/1968 | Mondiadis . |
| 3,742,952 | 7/1973 | Magers et al. . |
| 3,759,106 | 9/1973 | Wachter et al. ................. 73/864.34 |
| 3,875,941 | 4/1975 | Adair . |
| 4,040,299 | 8/1977 | Snyder ............................ 73/864.52 |
| 4,047,526 | 9/1977 | Reynolds et al. . |
| 4,191,054 | 3/1980 | Jacoby et al. ..................... 73/864.61 |

FOREIGN PATENT DOCUMENTS 572614 2/1976 Switzerland ..................... 73/864.62

Primary Examiner—S. Clement Swisher
Attorney, Agent, or Firm—Robert S. Beiser

[57] ABSTRACT

An improved apparatus for collecting atmospheric samples, particularly air samples, comprises a sealed collapsible receptacle which includes a hollow body having a base, top and side walls. At least the side walls are constructed of a flexible material. A venting mechanism introduces the atmosphere surrounding the apparatus into the receptacle at a controlled rate. The receptacle includes means for progressively expanding after being compressed. This progressive expansion creates a vacuum within the receptacle, thereby aspirating a measured volume of atmosphere per unit of time through the venting mechanism. Further provided are means for removing a desired quantity or sample of the retained atmosphere from the receptacle, as required.

18 Claims, 7 Drawing Figures

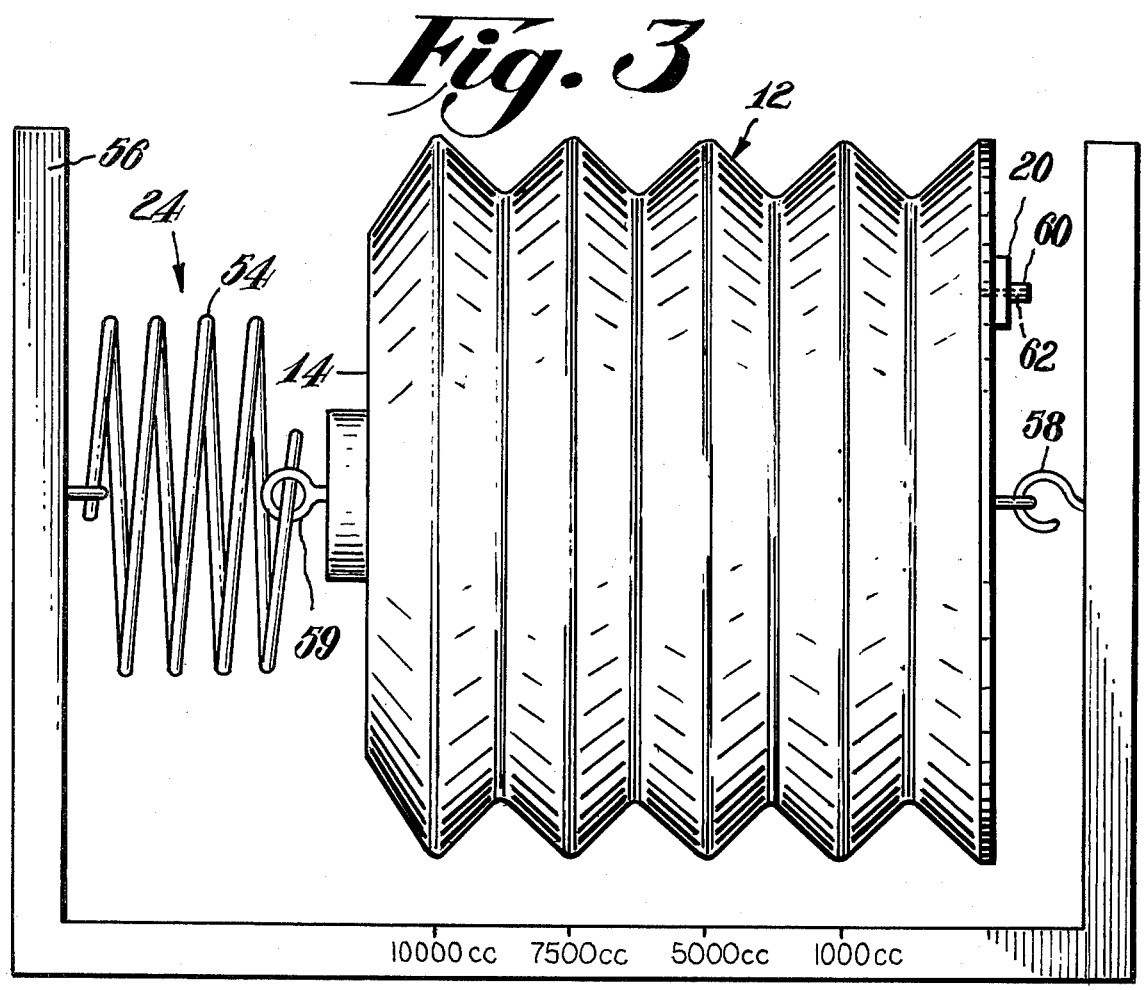
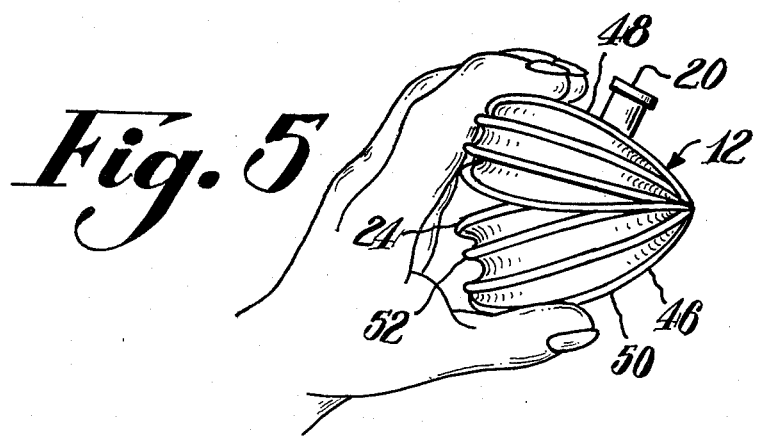

SAMPLING APPARATUS

BACKGROUND OF THE INVENTION

The present invention relates generally to devices for obtaining gaseous samples, and particularly to obtaining air samples.

In recent years the attention of the public has increasingly focused on the dangers of air pollution. Along these same lines, the government has established clean air standards which are administered by the Environmental Protection Agency and the Occupational Safety and Health Administration. In order to determine the presence and extent of harmful chemicals and particulate matter in the air, systematic and scientific sampling must be conducted.

One particular area of concern in recent years has been exposure by hospital operating room personnel to commonly used gaseous anesthetics. In order to prevent exposure to excessive levels of such anesthetics, several devices have been developed for sampling the atmosphere in hospital operating rooms. The samples obtained are chemically analyzed in order to determine the extent of such anesthetic contamination. Among such devices are those of Calibrated Instruments, Inc., and Boehringer Laboratories, which utilize a vacuum pump to inject a quantity of air within the operating room into a sample receptacle for later chemical analysis. However, several problems have remained in obtaining samples of operating room air. Primary among these is the fact that an electric pump is required to collect the air samples. The danger of explosion being extremely high in operating rooms due to the flammable nature of the anesthetic gases, such electrical devices must be shock proof, making them extremely expensive. In addition, such vacuum pumps tend to be expensive to operate either in the use of electricity or in batteries.

A recent improvement in atmospheric sampling apparatus may be found in U.S. Pat. No. 4,191,054 assigned to the assignee of the present invention, Air Test Labs, Inc. The aforementioned device utilizes the flow of liquid to create a vacuum thereby drawing atmospheric samples into a container. However, use of such a liquid is contraindicated when testing for water soluble particulate matter contained in the air.

Therefore, it is an object of the present invention to provide an apparatus for obtaining air samples which does not require the use of a moving liquid, which does not require the use of electric motors, and which is inexpensive and easy to use.

SUMMARY OF THE INVENTION

The present invention is an improved apparatus for collecting atmospheric samples, particularly air samples. The apparatus comprises a sealed collapsible receptacle, formed as a hollow body with a base, top and side walls. At least the side walls are constructed of a flexible material, and preferably the entire receptacle comprises a single collapsible, flexible material. Operatively associated with the receptacle is a venting mechanism which controllably introduces atmosphere from around the apparatus into the receptacle. Compression of the receptacle creates a negative pressure within it. Actuating means controllably and progressively expand the receptacle after it has been compressed, which maintains a vacuum therein. This vacuum is effective to aspirate a measured volume of atmosphere per unit of time through the venting mechanism and into the receptacle. Once a desired quantity of atmosphere is contained within the receptacle, a mechanism is further provided for removing a representative sample therefrom. In a preferred embodiment, the receptacle is constructed of a silicone elastomer. Alternatively, such a receptacle may be constructed of a latex rubber, a polyethylene or polypropylene.

In order to vent the aforementioned receptacle, in a preferred embodiment, a resilient, penetrable septum is sealed either upon or through the receptacle. A hollow needle is insertable through the septum so that the gaseous atmosphere about the receptacle may pass therein. The size of the orifice through the hollow needle member is one of the means by which the rate of flow of atmosphere into the receptacle may be controlled.

One means of actuating the expansion of the receptacle is through a series of resilient accordian pleats formed in the side walls of the receptacle. Due to the material of which the side walls are constructed, the accordian pleats are of sufficient resiliency to expand the receptacle to a substantially open position after it has been compressed. Alternatively, a series of corrugations may be formed in the side walls of the receptacle for accomplishing the same function.

An additional means of actuating the expansion of the receptacle is through the use of one or more resilient coil springs attached to the receptacle at one end, and to the base member at the other end. After the receptacle has been compressed, the coiled spring causes the receptacle to expand to a substantially open position. A more preferred embodiment comprises the containment of the resilient coiled spring within the side walls of the receptacle, so as to resiliently expand the receptacle after it has been compressed. When such a spring is used, the use of pleats or bellows is not required in the flexible side walls. Alternatively, the receptacle may be weighted at its base so as to controllably expand, when suspended from a hook. Again, pleats or corrugations are not required. A further alternative embodiment is the construction of the receptacle in the configuration of a bellows, sufficiently resilient to return to an expanded position after compression thereof.

In addition to a hollow needle, the previously mentioned venting mechanism may alternatively comprise a manually operable valve having an orifice of a known size contained therein, so that upon an opening of the valve, flow of air may be introduced at a controlled rate into the receptacle. The orifice in the valve member, or in the previously mentioned needle preferably comprises the same orifice size as a 27 gauge hypodermic needle. Through the use of such a known orifice size, and by selecting an actuating mechanism which expands the receptacle to an open configuration over a known period of time, a time weighted average sample may be obtained of the surrounding atmosphere, for chemical analysis purposes. In a preferred embodiment, the period of time required to fully open the receptacle from a complete compressed position is approximately 8 hours. However, other periods of time such as 4 hours, 16 hours or 24 hours may be provided simply by altering the size of the receptacle, the actuating means, or the size of the orifice.

The previously mentioned means for removing a sample from the receptacle may comprise a hypodermic syringe which is inserted into the receptacle or through the previously mentioned septum into the receptacle. Once inserted, a desired quantity of the atmosphere within the receptacle may be withdrawn. The syringe itself may then be used to inject the sample into a gas chromatograph, or the sample may be injected into a sealed vacuum tube.

The invention further includes a method of collecting atmospheric samples utilizing the aforementioned collection apparatus. The method comprises the steps of compressing the collapsible receptacle so as to evacuate same. The receptacle is then controllably vented with a known volume of air per unit of time. The resilient receptacle expands due to the previously mentioned actuating means, so as to maintain a negative pressure therein. Finally, once the receptacle is filled with air, the venting means are sealed so as to retain the atmosphere within the receptacle. The preferred method of venting the receptacle is by inserting a hollow needle of a desired orifice size into the receptacle or into a resilient rubber septum attached to the receptacle. In those cases when it is not desirable to directly inject the sample contained within the hypodermic syringe into a gas chromatograph, the syringe is injected into a sealed vacuum tube. The syringe is then withdrawn from the vacuum tube. When chemical analysis of the sample is available, another hypodermic syringe is injected into the sealed vacuum tube and a measured quantity of atmosphere from the vacuum tube is withdrawn into the syringe. This measured quantity is then injected into a gas chromatograph for chemical analysis.

BRIEF DESCRIPTION OF THE DRAWINGS

FIG. 3 of the drawings is a side view of an alternative embodiment of the improved atmospheric sample collecting apparatus shown in FIG. 1.

FIG. 5 of the drawings is a side view of an additional alternative embodiment of an improved atmospheric sampling apparatus.

DETAILED DESCRIPTION OF THE PREFERRED EMBODIMENT

Figure 1:
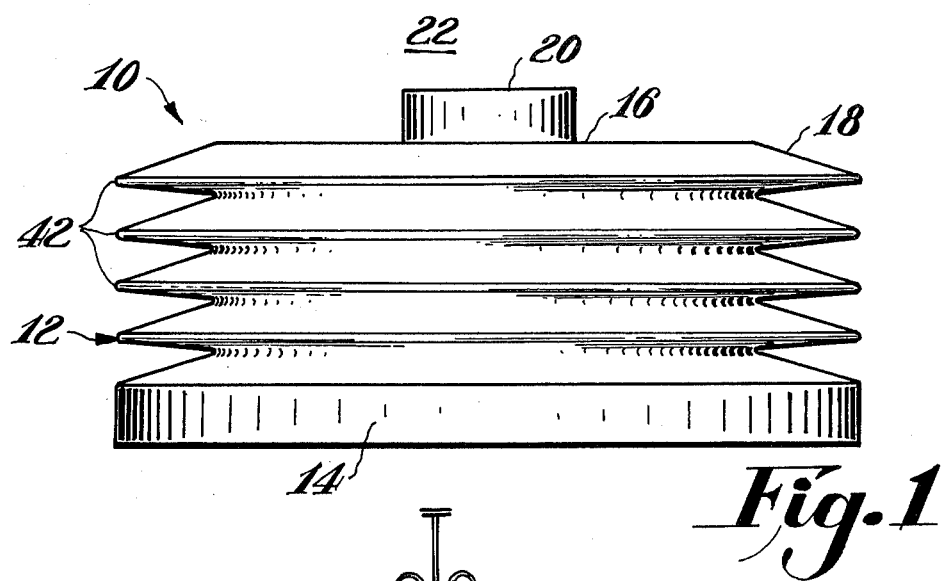
FIG. 1 of the drawings is a side view of an improved atmospheric sample collection device in a compressed configuration.

While this invention is susceptible of embodiment in many different forms, there is shown in the drawings and will herein be described in detail, several specific embodiments with the understanding that the embodiments illustrated are an exemplification of the principles of the invention, and are not intended to limit the invention to the embodiment illustrated.

As best seen in FIG. 1 of the drawings, improved apparatus 10 for collecting atmospheric samples comprises a sealed collapsible receptacle 12 which includes a hollow body comprising a base 14, a top 16, and side walls 18. Side walls 18 are constructed of a flexible material so as to be collapsible. Further included, as best seen in FIG. 2 of the drawings, is venting mechanism 20 which controllably introduces the atmosphere 22 surrounding the apparatus 10 into receptacle 12.

FIGS. 2 through 5 show a variety of actuating means 24 for controllably and progressively expanding receptacle 12 after compression thereof as shown in FIG. 1. This controlled and progressive expansion of receptacle 12 creates a vacuum within the receptacle so as to aspirate a measured volume of atmosphere per unit of time through venting means 20 and into receptacle 12.

Figure 2:
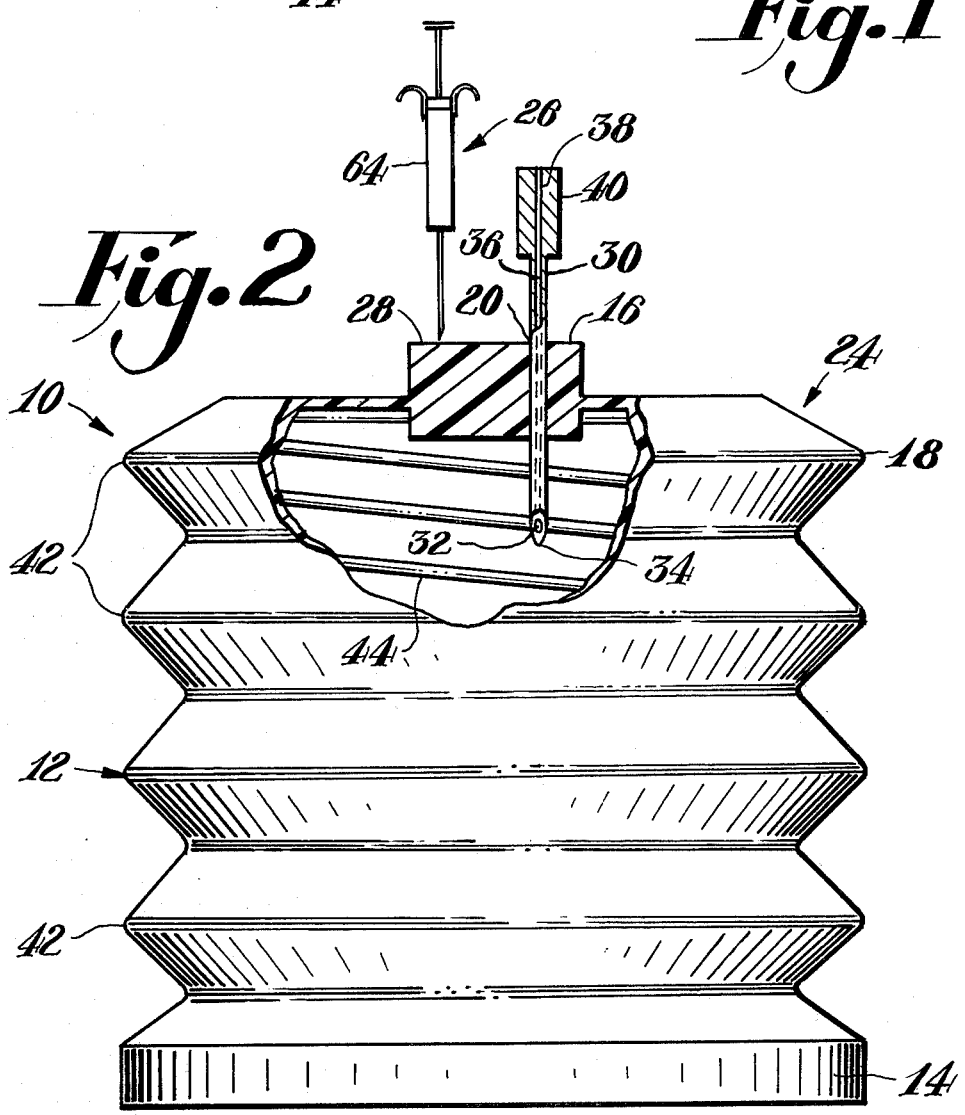
FIG. 2 of the drawings is a side view, partially cut away, of the improved atmospheric sampling apparatus of FIG. 1, showing in particular a coiled spring disposed about the side walls of the apparatus.

As best seen in FIG. 2 of the drawings, sample removal means 26 are further provided for withdrawing a desired quantity of retained atmosphere 22 from within receptacle 12. In FIG. 2, venting mechanism 20 comprises a plurality of resilient penetrable septums 28 fixedly attached and sealed to receptacle 12. A hollow needle 30 is used to penetrate septum 28. Hollow needle 30 has an orifice 32 proximate its sharpened tip 34 and a lumen 36 extending therethrough to a corresponding aperture 38 at proximal end 40 for the passage of air therethrough.

As further seen in FIGS. 1-5, receptacle 12 includes a multiplicity of accordian pleats 42 formed in side wall 18 of receptacle 12. Accordian pleats 42 and the material of which side wall 18 is formed, such as silicone rubber, are sufficiently resilient so as to expand receptacle 12 to a substantially open position, as shown in FIG. 2, from the compressed configuration shown in FIG. 1. Alternatively, not shown in the drawings, are a plurality of corrugations or sinusoidal undulations formed in the wall of receptacle 12 to accomplish the same resilient expanding function.

As further seen in FIG. 2 of the drawings, actuating means 24 preferably comprises one or more resilient coil springs 44 contained within and disposed about the side walls 18 of receptacle 12. Coil springs 44 are sufficiently resilient to expand receptacle 12 to a substantially open position, such as that shown in FIG. 2, from the compressed configuration shown in FIG. 1.

As best seen in FIG. 5 of the drawings, receptacle 12 may comprise a bellows 46 formed of resilient material of sufficient resiliency to return to a normal expanded position after compression. Bellows 46, as shown in FIG. 5, comprises a substantially flat top 48 and bottom 50 connected by a pleated side wall 52 constructed of resilient material. Resilient side wall 52 permits bellows 46 to be compressed and resiliently returned to its original configuration. Air is then drawn through venting means 20 into receptacle 12. Receptacle 12, as are all the embodiments shown, when compressed is reduced to minimum volume so as to create a substantial vacuum therein.

In an alternative configuration, as shown in FIG. 3, actuating means 24 may comprise a plurality of resilient coil springs 54 attached to and interposed between base member 56 and receptacle 12, for controllably and progressively expanding receptacle 12 to a substantially open position after the compression thereof. In the embodiment illustrated, base 56 is attached to receptacle 12 by means of hooking mechanism 58. Similarly, coil spring 54 is attached to receptacle 12 by means of loop 59 which contains a hole for the reception of coil spring 54 at the base 14 of receptacle 12. Base 56 further includes markings along its length to indicate the size and/or volume of air contained with receptacle 12.

Figure 4:
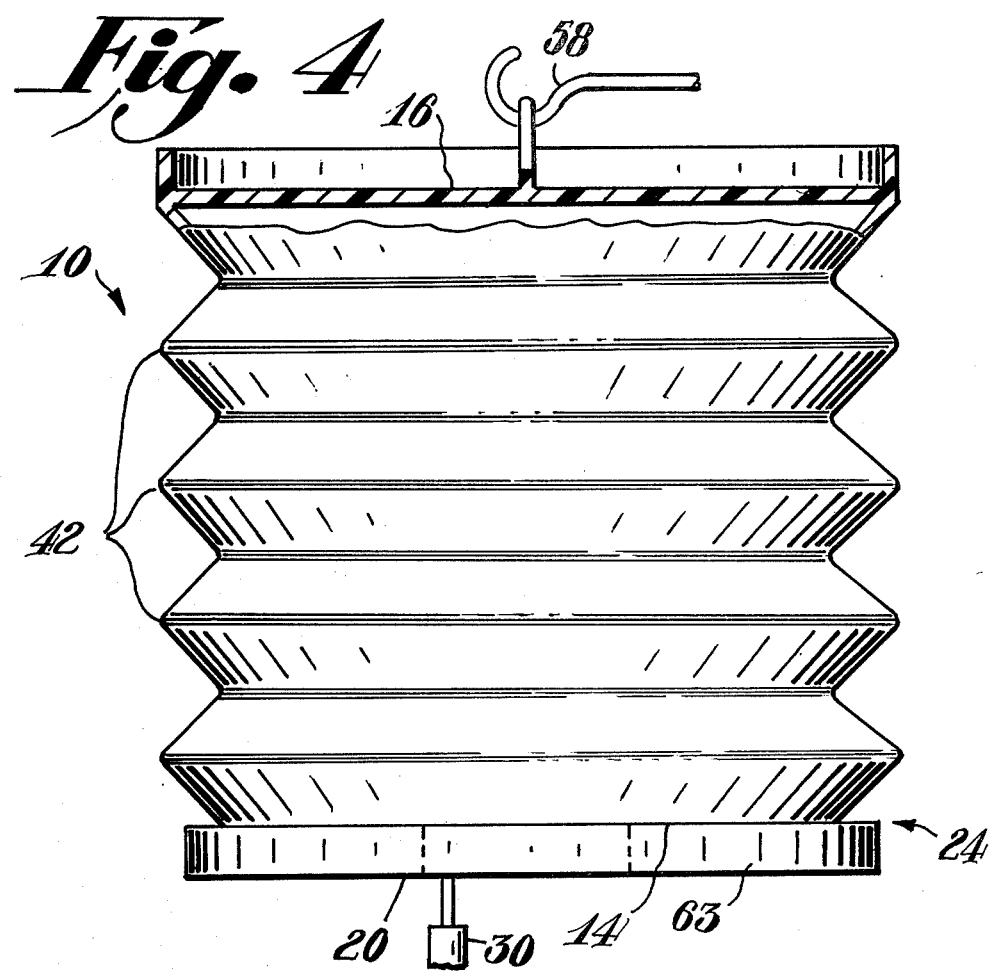
FIG. 4 of the drawings is a side view, partially broken away, of an additional alternative embodiment of an improved atmospheric sampling apparatus.

As best seen in FIG. 4 of the drawings, actuating means 24 may include base 14. Base 14 in the embodiment illustrated, is sufficiently weighted to controllably expand receptacle 12, thereby drawing air over a desired period of time through venting mechanism 20. Receptacle 12 is suspended from hook mechanism 58.

As further seen in FIG. 3, venting means 20 may comprise a manually operable valve member 60 which can be threadedly opened or closed to selectively allow passage of air through an orifice 62 extending through valve member 60. However, as seen in FIG. 2, in a preferred embodiment, venting means 20 comprises hollow needle 30, which preferably is a 27-gauge hypodermic needle, used for venting receptacle 12. By means of the known size of orifice 32 through hollow needle 30, the volume of receptacle 12 and the time required to fully expand it, a time weighted average sample may be obtained. Thus, for example, if a period of eight hours is required to fully expand receptacle 12, a sample may be withdrawn from the receptacle and the concentration of contaminants therein used to determine the average concentration of contaminants over an eight hour period.

Figure 6:
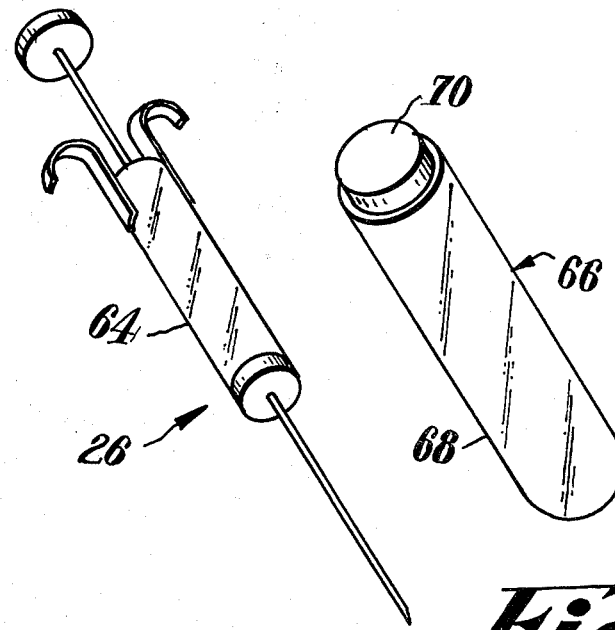
FIG. 6 of the drawings is a side view of a hypodermic syringe and sealed vacuum tube for use in obtaining atmospheric samples.

As further seen in FIGS. 2 and 6, in a preferred embodiment, sample removal means 26 comprises a hypodermic syringe 64 adapted for penetration of septum 28 and withdrawal of a desired quantity of atmosphere 22 from within receptacle 12. Alternatively, hypodermic syringe 64 may be inserted directly into resilient receptacle 12 and a sample withdrawn. In most cases, once the hypodermic syringe 64 has withdrawn a sample, the sample is then injected into sealed vacuum tube 66. Usually sealed vacuum tube 66 comprises a glass tube 68 with a resilient rubber septum 70 affixed at the top. Sealed vacuum tube 66 is suitable for mailing so that gas chromatographs testing can be conducted at a distant location from the site where atmosphere is being sampled.

As mentioned previously, resilient receptacle 12 preferably comprises a silicone elastomer or a latex rubber. However, equivalent materials such as polyethylene or polypropylene, preferably blow-molded, may be used to form receptacle 12. All of these materials provide the desired degree of resiliency, and excellent water and air barrier properties essential to an accurate sampling.

It should be further noted that actuating means 24, as seen in FIG. 4, may comprise a weight 63 at one end of receptacle 12 of sufficient mass to cause receptacle 12 to expand after being compressed and then suspended from hooking mechanism 58. The size of orifice 32 and the weight of weight 63 will control the rate at which receptacle 12 expands.

The invention further comprises a method for collecting atmospheric samples using the aforementioned equipment. The method comprises the steps of compressing collapsible receptacle 12 so as to evacuate the same. Atmosphere 22 is then controllably vented into receptacle 12 through venting mechanism 20. Due to actuating means 24, receptacle 12 is progressively expanded, which maintains a negative pressure therein, thus continuing to aspirate atmosphere 22 through venting mechanism 20 and into receptacle 12. When a desired period of time or quantity of sample has been obtained, venting mechanism 20 is sealed so as to retain atmosphere 22 within receptacle 12. As mentioned previously, the preferred means of venting receptacle 12 is through insertion of hollow needle 30 through either septum 28 or receptacle 12. The preferred means of withdrawing a representative quantity of atmosphere 22 from within receptacle 12 comprises inserting hypodermic syringe 64 into receptacle 12. A measured quantity of atmosphere 22 is then drawn into syringe 12 and this quantity may then be injected into a gas chromatograph for chemical analysis. Preferably, however, the measured quantity of sample is injected into sealed vacuum tube 66 wherein hypodermic syringe 64 is withdrawn from vacuum tube 66. Vacuum tube 66 may then be transported to a distant location where an additional hypodermic syringe is reinserted into sealed vacuum tube 66. A sample is then withdrawn by means of this additional hypodermic syringe and is inserted into a gas chromatograph for chemical analysis.

Figure 7:
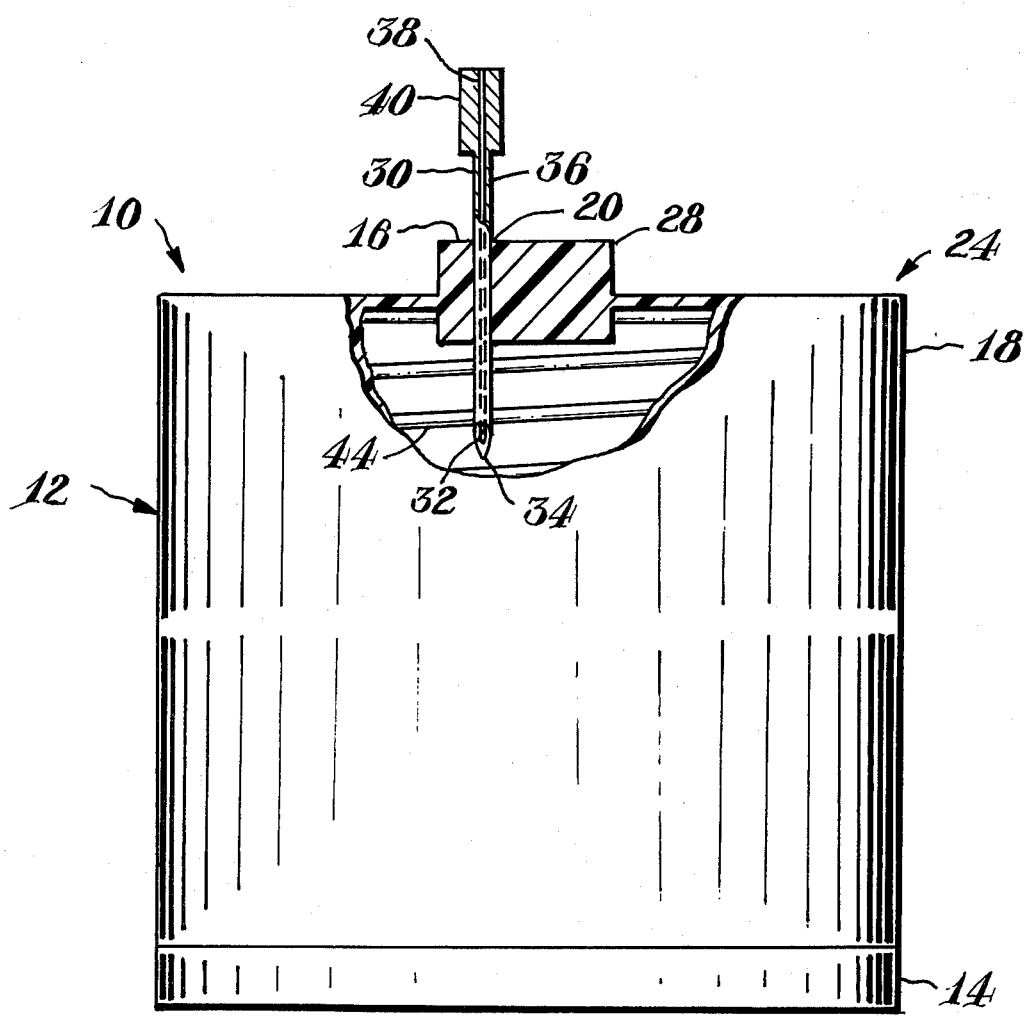
FIG. 7 of the drawings is a side view of an additional alternative embodiment of an improved atmosphere sampling apparatus.

As best seen in FIG. 7 of the drawings, when coil spring 44 is incorporated into side walls 18 of receptacle 12, accordion pleats 42 are not required. Actuation means 24 thus progressively expands receptacle 12 so as to vent the device by means of venting mechanism 20, for the desired period of time.

The foregoing description and drawings merely explain and illustrate the invention, and the invention is not limited thereto, except insofar as the appended claims are limited by those skilled in the art who have the disclosure before them and are able to make modifications and variations therein without departing from the scope of the invention.

I claim:

1. An improved apparatus for the collection of atmospheric samples comprising:
    a sealed manually collapsible receptacle including a hollow body comprising base and top elements and side walls, at least said side walls comprising a flexible thermoplastic or elasteromeric material sufficiently flexible to allow easy manual compression;
    venting means for the controlled introduction of the atmosphere surrounding said apparatus into said receptacle;
    said venting mean comprising one or more resilient penetrable septum members fixedly attached and sealed to said receptacle, and
    a hollow needle member having an aperture proximate its sharpened tip, said hollow needle member being insertable through said septum whereby gaseous atmosphere may pass into said receptacle; and
    actuating means for automatically, controllably and progressively expanding said receptacle after the compression thereof, said expansion thereby creating a vacuum in said receptacle, said controlled expansion being effective to aspirate a measured volume of atmosphere per unit of time through said venting means and into said receptacle; and
    sample removal means for permitting the withdrawal of a desired quantity of said retained atmosphere from within said receptacle, as required.

2. The invention according to claim 1 wherein said actuating means comprises a multiplicity of accordian pleats formed in said side walls of said receptacle, said side walls being of sufficient resiliency to expand said receptacle to a substantially open position after the compression thereof.

3. The invention according to claim 1 wherein said actuating means comprises a multiplicity of corrugations formed in said side walls of said receptacle, said side walls being of sufficient resiliency to expand said receptacle to a substantially open position after the compression thereof.

4. The invention according to claim 1 wherein said actuating means comprises a plurality of resilient coil spring members contained within and disposed about the side walls of said receptacle, said coil spring or springs being of sufficient resiliency to expand said receptacle to a substantially open position after the compression thereof.

5. The invention according to claim 1 wherein said actuating means comprises a plurality of resilient coil spring members attached to and interposed between a base member and said receptacle for the progressive expansion of said receptacle to a substantially open position after the compression thereof.

6. The invention according to claim 1 wherein said receptacle comprises a bellows formed of material of sufficient resiliency to return to a normal expanded position after compression thereof, said bellows comprising a hollow body having top and base elements connected by a pleated side wall constructed and arranged for the compression of said bellows to a condition of substantially minimum volume by collapsing of said side wall.

7. The invention according to claim 1 wherein said hollow needle comprises a 27-gauge hypodermic needle.

8. The invention according to claim 1 in which said apparatus provides time weighted average samples of said surrounding atmosphere for chemical analysis thereof.

9. The invention according to claim 8 in which said apparatus controllably draws a stream of said surrounding atmosphere into said apparatus for a period of substantially eight hours, thereby permitting withdrawal of an atmospheric sample having an average concentration of the chemicals present in said atmosphere over an eight hour period.

10. The invention according to claim 1 in which said sample removal means comprises a hypodermic syringe adapted for penetration and withdrawal of a desired quantity of the atmosphere to be sampled from said apparatus through one of said septums or through said receptacle.

11. The invention according to claim 10 in which said sample removal means further comprises a sealed vacuum tube member adapted for injection of said desired quantity of atmosphere by said hypodermic syringe and for the retention thereof.

12. The invention according to claim 1 or 3 or 7 in which said flexible material comprises a silicone elastomer.

13. The invention according to claim 1 or 3 or 7 in which said flexible material comprises a polyethylene or polypropylene.

14. A method for the collection of atmospheric samples utilizing a collection apparatus having a sealed collapsible receptacle including a hollow body comprising base and top elements and side walls, at least said side walls comprising a flexible material, actuating means for controllably and progressively expanding said receptacle after compression, venting means for the controlled introduction of the atmosphere surrounding said apparatus into said receptacle during said expansion, and base means for the support of said apparatus, said method comprising:
compressing said collapsible receptacle so as to evacuate same;
venting said receptacle so as to allow the controlled introduction of the atmosphere surrounding said apparatus into said receptacle said venting of said receptacle comprising inserting a hollow needle member into said receptacle;

automatically expanding said receptacle so as to maintain a negative pressure therein, thereby aspirating a desired quantity of air into said receptacle; and
sealing said venting means upon said receptacle being expanded for a desired period of time.

15. The invention according to claim 14 including the additional steps of:
inserting a hypodermic syringe into said receptacle;
drawing a measured quantity of said atmosphere into said syringe; and
injecting said measured quantity of said atmosphere into a gas chromatograph for chemical analysis thereof.

16. The invention according to claim 14 including the additional steps of:
inserting a hypodermic syringe into said receptacle;
injecting said measured quantity of said atmosphere into a sealed vacuum tube and withdrawing said syringe;
transporting said vacuum tube to the location of a gas chromatograph;
injecting a hypodermic syringe into said sealed vacuum tube;
drawing a measured quantity of said atmosphere into said syringe; and
injecting said measured quantity of said atmosphere into a gas chromatograph for chemical analysis thereof.

17. An improved apparatus for the collection of atmospheric samples comprising:
a sealed manually collapsible receptacle including a hollow body comprising base and top elements and side walls, at least said side walls comprising a flexible thermoplastic or elasteromeric material sufficiently flexible to allow easy manual compression;
venting means for the controlled introduction of the atmosphere surrounding said apparatus into said receptacle;
actuating means for automatically, controllably and progressively expanding said receptacle after the compression thereof, said expansion thereby creating a vacuum in said receptacle, said controlled expansion being effective to aspirate a measured volume of atmosphere per unit of time through said venting means and into said receptacle;
sample removal means for permitting the withdrawal of a desired quantity of said retained atmosphere from within said receptacle, as required;
said actuating means comprising a plurality of resilient coil spring members attached to and interposed between a base member and said receptacle for the progressive expansion of said receptacle to a substantially open position after the compression thereof; and
said base member further comprises marking means uniformly disposed along its length for providing alpha-numeric indicia of the size of and volume of air contained within said receptacle.

18. An improved apparatus for the collection of atmospheric samples comprising:
a sealed manually collapsible receptacle including a hollow body comprising base and top elements and side walls, at least said side walls comprising a flexible thermoplastic or elasteromeric material sufficiently flexible to allow easy manual compression;

venting means for the controlled introduction of the atmosphere surrounding said apparatus into said receptacle;

actuating means for automatically, controllably and progressively expanding said receptacle after the compression thereof, said expansion thereby creating a vacuum in said receptacle, said controlled expansion being effective to aspirate a measured volume of atmosphere per unit of time through said venting means and into said receptacle;

said actuating means comprising; suspension means for suspending said receptacle at a first end;

weight means adjacent the second end of said receptacle for controllably drawing said receptacle open by means of gravitational force; and sample removal means for permitting the withdrawal of a desired quantity of said retained atmosphere from within said receptacle, as required.

* * * * *